United States Patent [19]

Habicht et al.

[11] 4,322,431
[45] Mar. 30, 1982

[54] PHARMACEUTICAL PREPARATIONS CONTAINING BENZIMIDAZOLE 2-DERIVATIVES

[75] Inventors: Ernst Habicht, Oberwil; Pier G. Ferrini, Binningen; Alfred Sallmann, Bottmingen, all of Switzerland

[73] Assignee: Ciba-Geigy Corporation, Ardsley, N.Y.

[21] Appl. No.: 116,138

[22] Filed: Jan. 28, 1980

[30] Foreign Application Priority Data

Feb. 9, 1979 [CH] Switzerland .................. 1291/79

[51] Int. Cl.³ ............................................. A61K 31/415
[52] U.S. Cl. ................................ 424/273 B; 424/263; 548/331
[58] Field of Search .................. 424/273 B; 548/331

[56] References Cited

U.S. PATENT DOCUMENTS 4,141,982  2/1979  Habicht et al. .................. 424/267

FOREIGN PATENT DOCUMENTS 766749  1/1957  United Kingdom .

OTHER PUBLICATIONS

J. Chem. Soc., (c), 1969, 70–74.
Chemical Abstracts 73:25359 u, (1970).

*Primary Examiner*—Leonard Schenkman
*Attorney, Agent, or Firm*—Prabodh I. Almaula

[57] ABSTRACT

Benzimidazole 2-derivatives that are acylated in the nucleus and have the formula

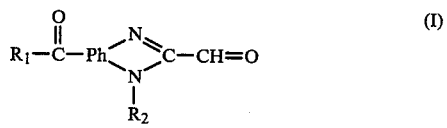

in which
$R_1$ represents an aliphatic, cycloaliphatic, aromatic, araliphatic, heterocyclic or heterocyclic-aliphatic radical,
$R_2$ represents hydrogen or an aliphatic radical, and
Ph represents a 1,2-phenylene group containing the radical $R_1-C(=O)-$, have anti-allergic properties, serve as medicaments and can be used as medicinal active substances in pharmaceutical preparations.

9 Claims, No Drawings

PHARMACEUTICAL PREPARATIONS CONTAINING BENZIMIDAZOLE 2-DERIVATIVES

The invention relates to pharmaceutical preparations containing a benzimidazole 2-derivative that is acylated in the nucleus and has the formula

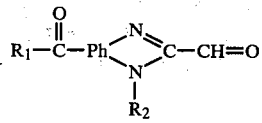

in which
- $R_1$ represents an aliphatic, cycloaliphatic, aromatic, araliphatic, heterocyclic or heterocyclic-aliphatic radical,
- $R_2$ represents hydrogen or an aliphatic radical, and
- Ph represents a 1,2-phenylene group containing the radical $R_1-C(=O)-$, and their use as active substances in medicaments.

In context of the present description, organic radicals and compounds that are termed "lower" contain especially up to and including 7 carbon atoms, but preferably up to and including 4 carbon atoms.

Aliphatic, cycloaliphatic, aromatic and araliphatic radicals $R_1$ and $R_2$ are especially optionally substituted aliphatic, cycloaliphatic, aromatic or araliphatic hydrocarbon radicals, such as the corresponding lower alkyl, lower alkenyl, cycloalkyl, phenyl, naphthyl or phenyl-lower alkyl radical. Substituents especially of lower alkyl $R_1$ and lower alkyl $R_2$, are, for example, hydroxy, lower alkoxy, lower alkylthio or phenylthio, lower alkylsulphinyl or phenylsulphinyl, or lower alkylsulphonyl or phenylsulphonyl, or, especially of phenyl or phenyl-lower alkyl $R_1$, lower alkyl, lower alkoxy and/or halogen. Heterocyclyl in a heterocyclic or heterocyclic-aliphatic radical $R_1$ is especially monocyclic heterocyclyl of aromatic nature, with one hetero atom, such as oxygen, sulphur or nitrogen, as ring member, such as furyl, thienyl or pyridyl. In a heterocyclic-aliphatic radical $R_1$ the aliphatic moiety is, for example, a corresponding aliphatic hydrocarbon radical, especially lower alkyl.

In addition to being substituted by the radical of the formula $R_1-C(=O)-$ 1,2-phenylene may additionally be substituted one or more times inter alia by lower alkyl, lower alkoxy, hydroxy and/or halogen.

Lower alkoxy means, for example, methoxy, ethoxy, n-propoxy, isopropoxy, n-butoxy, isobutoxy, tert.-butoxy, n-pentyloxy or n-hexyloxy.

Phenyl-lower alkoxy is, for example, benzyloxy or 1- or 2-phenylethoxy.

Hydroxy-lower alkoxy, lower alkoxy-lower alkoxy or di-lower alkylamino-lower alkoxy is especially 2- or 3-hydroxy-lower alkoxy, for example 2-hydroxyethoxy, 3-hydroxypropoxy, or 2,3-dihydroxypropoxy, or 2- or 3-lower alkoxy-lower alkoxy, for example 2-methoxyethoxy, 2-ethoxyethoxy or 3-methoxypropoxy, or di-lower alkylamino-lower alkoxy, for example dimethylaminoethoxy or diethylaminoethoxy.

Lower alkyl is, for example, methyl, ethyl, n-propyl, isopropyl, n-butyl, isobutyl, tert.-butyl, n-pentyl, n-hexyl or n-heptyl.

Halogen is especially halogen of an atomic number of up to and including 35, that is to say, fluorine, chlorine or bromine.

Lower alkylene is, for example, 1,4-butylene, 1,5-pentylene or 1,6-hexylene.

Lower alkenyl is, for example, vinyl, 1-methylvinyl, 1-ethylvinyl, allyl, 2- or 3-methylallyl or 3,3-dimethylallyl.

Cycloalkyl contains preferably 3 to 8 ring atoms and is, for example, cyclopropyl, cyclopentyl, cyclohexyl, cycloheptyl or cyclooctyl.

Lower alkylthio is, for example, methylthio or ethylthio, while lower alkylsulphinyl and lower alkylsulphonyl represent, for example, methylsulphinyl, ethylsulphinyl, methylsulphonyl or ethylsulphonyl.

Lower alkyl that is substituted by lower alkylthio, lower alkylsulphinyl or lower alkylsulphonyl is, for example, methylthiomethyl or ethylthiomethyl, 1- or 2-methylthioethyl or 1- or 2-ethylthioethyl, or 2- or 3-methylthiopropyl or 2- or 3-ethylthiopropyl, methylsulphinylmethyl or ethylsulphinylmethyl, 1- or 2-methylsulphinylethyl or 1- or 2-ethylsulphinylethyl, or 2- or 3-methylsulphinylpropyl or 2- or 3-ethylsulphinylpropyl, or methylsulphonylmethyl or ethylsulphonylmethyl, 1- or 2-methylsulphonylethyl or 1- or 2-ethylsulphonylethyl, or 2- or 3-methylsulphonylpropyl or 2- or 3-ethylsulphonylpropyl. Lower alkyl that is substituted by phenylthio, phenylsulphinyl or phenylsulphonyl is, for example, phenylthiomethyl, phenylsulphinylmethyl or phenylsulphonylmethyl, or 1- or 2-phenylthioethyl, 1- or 2-phenylsulphinylethyl or 1- or 2-phenylsulphonylethyl.

Phenyl-lower alkyl is, for example, benzyl, 1- or 2-phenylethyl or 1-, 2- or 3-phenylpropyl.

Furyl is, for example, 2-furyl, and thienyl, for example, 2-thienyl, while pyridyl can be 2-, 3- or 4-pyridyl.

Furyl-lower alkyl, thienyl-lower alkyl and pyridyl-lower alkyl are especially correspondingly substituted methyl radicals, such as furfuryl, 2-thenyl or picolyl, for example, 2- or 4-pyridylmethyl.

The compounds of the formula I exhibit valuable pharmacological properties. In particular, they have an anti-allergic action, which may be demonstrated, for example, in rats, at doeses from approximately 0.03 to approximately 10 mg/kg when administered intravenously and in doses from approximately 1 to approximately 100 mg/kg when administered orally in a passive cutaneous anaphylaxis test (PCA reaction), which is carried out analogously to the method described by Goose and Blair, Immunology, Vol. 16, p. 749 (1969). The passive cutaneous anaphylaxis is produced in accordance with the process described by Ovary, Progr. Allergy, Vol. 5, p. 459 (1958). The antiallergic, and especially the degranulation-inhibiting, action can also be observed in vitro by way of the release of histamine from peritoneal cells of the rat in the dosage range of from approximately 0.1 to approximately 100 μg/ml in the case of immunologically-induced release, (for which, for example, rats infected with *Nippostrongilus brasiliensis*, are used), and in the dosage range of from approximately 1.0 to approximately 100 μg/ml in the case of chemically-induced release (brought about for example by a polymer of N-4-methoxyphenylethyl-N-methylamine). The compounds of the present invention may consequently be used as inhibitors of allergic reactions, for example in the treatment and prophylaxis of allergic disorders, such as asthma, extrinsic as well as intrinsic asthma, or as inhibitors of other allergic disorders, such as allergic rhinitis, for example hay fever, conjunctivitis, or allergic dermatitis, for example urticaria or eczemas.

The invention relates especially to compounds of the formula I in which $R_1$ represents lower alkyl optionally substituted by lower alkoxy, lower alkylthio, lower alkylsulphinyl, lower alkylsulphonyl, phenylthio, phenylsulphinyl or phenylsulphonyl; lower alkenyl or cycloalkyl; or phenyl or phenyl-lower alkyl both optionally substituted in the phenyl moiety by lower alkyl, lower alkoxy or halogen; or furyl, thienyl or pyridyl; or furyl-lower alkyl, thienyl-lower alkyl or pyridyl-lower alkyl; $R_2$ represents hydrogen or lower alkyl, and Ph represents 1,2-phenylene containing the radical of the formula $R_1-C(=O)-$ and optionally substituted by lower alkyl, lower alkoxy, hydroxy and/or halogen, as medicaments, their use as active substances in medicaments and pharmaceutical preparations containing them.

The invention relates especially to compounds of the formula I, in which $R_1$ represents lower alkyl having up to and including 7 carbon atoms, for example methyl, ethyl, n-propyl, isopropyl, n-butyl, isobutyl, tert.-butyl, n-pentyl, neopentyl, n-hexyl or n-heptyl; lower alkoxy-lower alkyl, lower alkylthio-lower alkyl, lower alkyl-sulphinyl-lower alkyl or lower alkylsulphonyl-lower alkyl, in which the individual lower alkyl radicals contain up to and including 4 carbon atoms, for example methoxymethyl, ethoxymethyl, methylthiomethyl, ethylthiomethyl, methylsulphinylmethyl, ethylsulphinylmethyl, methylsulphonylmethyl or ethylsulphonylmethyl, 1- or 2-methoxyethyl, 1- or 2-ethoxyethyl, 1- or 2-methylthioethyl, 1- or 2-ethylthioethyl, 1- or 2-methylsulphinylethyl, 1- or 2-ethylsulphinylethyl, 1- or 2-methylsulphonylethyl or 1- or 2-ethylsulphonylethyl, or 1-, 2- or 3-methoxypropyl, 1-, 2- or 3-ethoxypropyl, 1-, 2- or 3-methylthiopropyl, 1-, 2- or 3-ethylthiopropyl, 1-, 2- or 3-methylsulphinylpropyl, 1-, 2- or 3-ethylsulphinylpropyl, 1-, 2- or 3-methylsulphonylpropyl or 1-, 2- or 3-ethylsulphonylpropyl; phenylthio-lower alkyl, phenylsulphinyl-lower alkyl or phenylsulphonyl-lower alkyl, in which the lower alkyl radical contains up to and including 4 carbon atoms, for example phenylthiomethyl, phenylsulphinylmethyl or phenylsulphonylmethyl, 1- or 2-phenylthioethyl, 1- or 2-phenylsulphinylethyl or 1- or 2-phenylsulphonylethyl, or 1-, 2- or 3-phenylthiopropyl, 1-, 2- or 3-phenylsulphinylpropyl or 1-, 2- or 3-phenylsulphonylpropyl; lower alkenyl having up to and including 5 carbon atoms, for example 1-methylvinyl or 1-ethylvinyl, or allyl; cycloalkyl having up to and including 7 carbon atoms, for example cyclopropyl or cyclohexyl; phenyl or phenyl-lower alkyl having up to and including 4 carbon atoms in the lower alkyl radical and optionally substituted by lower alkyl and having up to and including 4 carbon atoms, for example methyl, lower alkoxy having up to and including 4 carbon atoms, for example methoxy, and/or halogen of an atomic number of up to and including 35, for example chlorine or bromine, for example benzyl or 1- or 2-phenylethyl; furyl, thienyl or pyridyl, for example 2-furyl, 2-thienyl or 2-, 3- or 4-pyridyl, or furyl-lower alkyl, thienyl-lower alkyl or pyridyl-lower alkyl having up to and including 4 carbon atoms in the lower alkyl radical, for example furfuryl, 2-thenyl or 2- or 4-picolyl; $R_2$ represents hydrogen or lower alkyl having up to and including 4 carbon atoms, for example methyl, and Ph represents 1,2-phenylene that contains the radical of the formula $R_1-C(=O)-$ and is optionally substituted by lower alkyl having up to and including 4 carbon atoms, for example methyl, lower alkoxy having up to and including 4 carbon atoms, for example methoxy, hydroxy and/or halogen having an atomic number of up to and including 35, for example chlorine or bromine, the radical of the formula $R_1-C(=O)-$ occupying any position that is suitable for substitution, preferably the 4- or 5-position of the 1,2-phenylene radical, as medicaments, their use as active substances in medicaments and pharmaceutical preparations containing them.

The invention relates especially to compounds of the formula

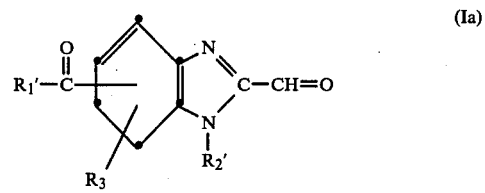

(Ia)

in which
$R_1'$ represents especially lower alkyl having up to and including 7 carbon atoms, for example methyl, ethyl, n-propyl, n-butyl, tert.-butyl, n-pentyl, n-hexyl or n-heptyl; also lower alkoxy-lower alkyl, lower alkylthio-lower alkyl, lower alkylsulphinyl-lower alkyl, phenylthio-lower alkyl or phenylsulphinyl-lower alkyl, in which the lower alkyl radicals contain up to and including 4 carbon atoms, for example methoxymethyl, methylthiomethyl, methylsulphinylmethyl, phenylthiomethyl or phenylsulphinylmethyl, 2-methoxyethyl, 2-methylthioethyl, 2-methylsulphinylethyl, 2-phenylthioethyl or 2-phenylsulphinylethyl, or 3-methoxypropyl, 3-methylthiopropyl, 3-methylsulphinylpropyl, 3-phenylthiopropyl or 3-phenylsulphinylpropyl; cycloalkyl having up to and including 6 ring carbon atoms, for example cyclopropyl or cyclohexyl; phenyl; furyl or pyridyl, for example 3- or 4-pyridyl;

$R_2'$ represents hydrogen or lower alkyl having up to and including 4 carbon atoms, for example methyl, and $R_3$ represents hydrogen, lower alkyl having up to and including 4 carbon atoms, for example methyl, lower alkoxy having up to and including 4 carbon atoms, for example methoxy, hydroxy or halogen having an atomic number of up to and including 35, for example chlorine, wherein the radical of the formula $R_1'-C(=O)-$ and the group $R_3$, if this is different from hydrogen, may occupy any position of the benzimidazole ring that is suitable for substitution, preferably the 5-position and the 6-position, as medicaments, their use as active substances in medicaments and pharmaceutical preparations containing them.

The invention relates especially to compounds of the formula Ia, in which $R_1'$ represents lower alkyl having up to and including 7 carbon atoms, for example up to and including 4 carbon atoms, for example methyl, ethyl, n-propyl, isopropyl or n-butyl, and $R_2'$ and $R_3$ represent lower alkyl having up to and including 4 carbon atoms, for example methyl, the radical $R_1'-C(=O)-$ occupying the 5-position of the benzimidazole ring and the lower alkyl radical $R_3$ occupying the 6-position of the benzimidazole ring, as medicaments, their use as active substances in medicaments and pharmaceutical preparations containing them.

The invention relates particularly to the use of the compounds of the formula I mentioned in the Examples, and pharmaceutical preparations containing them.

The compounds of formula I can be prepared in a manner known per se. They may be obtained, for example, by the process in which, in a compound of the formula II

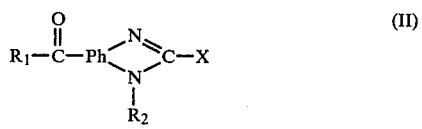

in which

X represents a radical that can be converted into the formyl group by oxidation or hydrolysis, X is converted into the formyl group by oxidation or hydrolysis.

A radical that can be converted into formyl by oxidation is especially the hydroxymethyl group and a radical that can be converted into formyl by hydrolysis is especially an acylalised or acetalised formyl group, such as esterified or etherified dihydroxymethyl, for example, dihalomethyl such as dichloromethyl, or lower alkylenedioxymethyl or di-lower alkoxymethyl, such as propylenedioxymethyl, or diethoxymethyl or dimethoxymethyl.

The oxidation is carried out preferably by reaction with manganese dioxide in chloroform at from approximately 0° to 50° C., preferably at from approximately 10° to 30° C. The hydrolysis of an acylalised formyl group, for example of dichloromethyl, is carried out preferably in aqueous ethanol in the presence of sodium acetate at from approximately 40° to 120° C., especially from 60° to 100° C., while an acetalised formyl group is preferably hydrolised in aqueous dioxan in the presence of dilute hydrochloric acid.

The compounds of the formula II to be used as starting substances can be obtained, for example, by reacting a compound of the formula

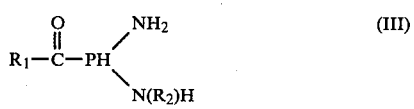

or a salt thereof, such as the hydrochloride thereof, with a compound of the formula

in which

X represents hydroxymethyl or an acylalised formyl group, for example, a dihalomethyl group, and, if desired, in the resulting compound, converting an acylalised formyl group X into acetalised formyl by reacting with a corresponding alkali metal alcoholate, for example sodium ethoxide.

The pharmaceutical preparations of the present invention, which contain compounds of the formula I. The pharmaceutical preparations according to the invention are for enteral administration, such as oral, nasal or rectal administration or for parenteral or topical administration to warm-blooded animals, and the preparations contain the pharmacological active substance alone or together with a pharmaceutically acceptable carrier. The dosage of the active substance depends on the species of warm-blooded animal, the age and the individual condition and on the method of administration.

Pharmaceutical preparations according to the invention are, for example, in unit dosage form, such as dragées, tablets, capsules or suppositories, or also ampoules, or in the form of inhalation preparations and pharmaceutical formulations for topical or local use, (for example, for insufflation). The new pharmaceutical preparations contain, for example, up to approximately 95% of active substance; the solid forms of administration such as dragées, tablets, capsules, suppositories and insufflation preparations contain, for example, from approximately 5 to approximately 90%, especially from approximately 10 to 60%, of the active substance, and injection ampoules and inhalation preparations contain, for example, from approximately 0.5 to approximately 20%, especially from approximately 1 to 10%, and very especially from approximately 1 to 5% by weight, of the active substance.

The pharmaceutical preparations of the present invention are prepared in a manner known per se, for example by means of conventional mixing, granulating, dragee-making, dissolving or lyophilising processes.

Pharmaceutical preparations for oral application may, for example, by obtained by combining the active substance with solid carriers, optionally granulating the resulting mixture and processing the mixture or granulate, if desired or necessary, after the addition of suitable auxiliaries, to form tablets or dragée cores. Suitable carriers are especially fillers, such as sugars, for example lactose, saccharose, mannitol or sorbitol, cellulose preparations and/or calcium phosphates, for example tri-calcium phosphate or calcium hydrogen phosphate; also binders, such as starch pastes using, for example, maize, wheat, rice or potato starches, gelatin, tragacanth, methylcellulose and/or polyvinylpyrrolidone; and/or, if desired, distintegrating agents, such as the above-mentioned starches; carboxymethyl starches, transversely cross-linked polyvinylpyrrolidone, agar, alginic acid or a salt thereof, such as sodium alginate. Auxiliaries are especially flow regulators and lubricants, for example silica, talc, stearic acid or salts thereof, such as magnesium or calcium stearate, and/or polyethylene glycol. Dragée cores are provided with suitable coatings that are optionally resistant to gastric juice, for which there are used, inter alia, concentrated sugar solutions that optionally contain gum arabic, talc, polyvinylpyrrolidone, polyethylene glycol and/or titanium dioxide, coating solutions in suitable organic solvents or solvent mixtures, or, for the preparation of coatings resistant to gastric juice, solutions of suitable cellulose preparations, such as acetyl cellulose phthalate or hydroxypropylmethylcellulose phthalate. Colourants or pigments may be added to the tables or dragée coatings, for example to identify or characterise different doses of active substance.

Other pharmaceutical preparations that may be administered orally are push-fit capsules made of gelatin, and also soft, sealed capsules consisting of gelatin and a plasticiser, such as glycerin or sorbitol. The push-fit capsules may contain the active substance in the form of a granulate, for example in admixture with fillers, such as lactose, binders, such as starches, and/or lubricants, such as talc or magnesium stearate, and optionally stabilisers.

In soft capsules, the active substance is preferably dissolved or suspended in suitable liquids, such as fatty oils, paraffin oil or liquid polyethylene glycols, and stabilisers may likewise be added.

Pharmaceutical preparations for rectal administration are, for example, in the form of suppositories consisting of a combination of the active substance and a suppository base substance. Suitable base substances for suppositories are, for example, natural or synthetic triglycerides, paraffin hydrocarbons, polyethylene glycols and higher alkanols. It is also possible to use gelatin rectal capsules that contain a combination of the active substance and a base substance. Suitable base substances are, for example, liquid triglycerides, polyethylene glycols and paraffin hydrocarbons.

For parenteral administration aqueous solutions of the active substance in water-soluble form, for example in the form of a water-soluble salt, are especially suitable; also suitable are suspensions of the active substance, such as corresponding oily injection suspensions, for which suitable lipophilic solvents or vehicles, such as fatty oils, for example sesame oil or synthetic fatty acid esters, for example ethyl oleate or triglycerides are used; or aqueous injection suspensions that contain substances increasing viscosity, for example sodium carboxymethylcellulose, sorbitol and/or dextran and, optionally, stabilisers.

Inhalants for the treatment of the respiratory passages by nasal or buccal administration are, for example, in the form of aerosols, sprays or insufflation capsules, which are able to distribute the pharmacological active substance in the form of a powder or in the form of drops of a solution or suspension. Preparations with powder-distributing properties usually contain, in addition to the active substance, a liquid propellant gas having a boiling point below room temperature and, if desired, carriers, such as liquid or solid, non-ionic or anionic, surfactants and/or solid diluents. Preparations in which the pharmacological active substance is present in solution contain, in addition thereto, a suitable propellant, and also if necessary, an additional solvent and/or a stabiliser. Instead of the propellant gas, compressed air may be used, and this can be produced by means of a suitable compression and decompression device as required.

Pharmaceutical preparations for topical and local use are, for example for treatment of the skin, in the form of lotions or creams that contain a liquid or semi-solid oil-in-water or water-in-oil emulsion, and salves (optionally containing a preservative); for treatment of the eyes, in the form of eye drops that contain the active compound in aqueous or oily solution and eye salves, which are preferably manufactured in sterile form; for the treatment of the nose, in the form of powders, aerosols and sprays, (similarly to those described above for the treatment of the respiratory passages), and also coarse powders, which are administered by rapid inhalation through the nostrils, and nose drops that contain the active compound in aqueous or oily solution; or for the local treatment of the mouth, lozenges that contain the active compound in a composition generally consisting of sugar and gum arabic or tragacanth, to which flavouring substances may be added, and also pastilles that contain the active substance in an inert composition consisting, for example, of gelatin and glycerin or sugar and gum arabic.

The invention likewise relates to the use of the new compounds of the formula I or salts thereof as pharmcologically active compounds, especially as anti-allergic agents, preferably in the form of pharmaceutical preparations. The daily dose administered to a warm-blooded animal of about 70 kg body weight is dependent on the form of application. For oral administration, daily doses of approximately 50 to approximately 500 mg, preferably from approximately 75 to 250 mg, are recommended, if desired divided into several individual doses during the day, for example into 1 to 4 individual doses.

The following Examples illustrate the above-described invention: they are not, however, intended to restrict its scope in any way. Temperatures are given in degrees Centigrade.

EXAMPLE 1

25 g of manganese dioxide are activated in 200 ml of alcohol-free chloroform for 2 hours by azeotropic dehydration. The solution is cooled, whilst stirring, to 10° C., 4.92 g of 5-butyryl-1,6-dimethylbenzimidazole-2-methanol are added and the whole is allowed slowly to return to room temperature and is stirred for 18 hours at room temperature. The solution is filtered, the filtrate evaporated to dryness and the residue recrystallised from chloroform/petroleum ether. 5-butyryl-1,6-dimethylbenzimidazole-2-carboxaldehyde having a melting point of 116.5°–118° is obtained.

The starting material may be prepared, for example, as follows:

A mixture of 24.1 g of 4-chloro-2-methyl-5-nitrobutyrophenone and 250 ml of a 33% solution of methylamine in ethanol is allowed to stand at room temperature; the crystalline starting material dissolves slowly, producing a yellow colouring. The reaction is slightly exothermic; the solution is therefore cooled with a water bath to prevent too much methylamine escaping. After 20 minutes, the starting material has completely dissolved and a precipitate then begins to form. The solution is allowed to stand for 16 hours at room temperature and then evaporated to dryness under reduced pressure. Diethyl ether (approximately 1000 ml), ice and sodium carbonate are added to the residue, the whole is shaken thoroughly and the organic layer separated off. This is washed twice with water and the aqueous solution is washed with diethyl ether. The combined organic solutions are dried over sodium sulphate, filtered and concentrated by evaporation to a volume of approximately 300 ml, then diluted with 100 ml of petroleum ether and cooled. The yellow, crystalline 2-methyl-4-methylamino-5-nitrobutyrophenone precipitates, is filtered off, washed with petroleum ether and dried in the air. Melting point 107°–108°.

A solution of 4.7 g of 2-methyl-4-methylamino-5-nitrobutyrophenone in 40 ml of dioxan is diluted with water and heated to reflux, and then, within a period of 10 minutes, is treated with a solution of 16 g of sodium dithionite in 70 ml of water causing the yellow colour of the reaction mixture of fade. The mixture is refluxed for a further 15 minutes, the pH is adjusted to 3 by the addition of approximately 30 ml of 6 N hydrochloric acid, and the mixture is refluxed for another 15 minutes, during which time sulphur dioxide escapes. The pH of the reaction mixture is adjusted to 2, again refluxed for approximately 5 minutes and the dioxan is evaporated off under reduced pressure. The hydrochloride of 5-amino-2-methyl-4-methylaminobutyrophenone precipitates out of the solution remaining; the suspension is cooled, rendered alkaline with concentrated sodium hydroxide solution and extracted with chloroform. The organic extract is washed twice with water, dried, filtered and concentrated by evaporation. The 5-amino-2-methyl-4-methylaminobutyrophenone melts at 126°–128°.

The conversion of 4-chloro-2-methyl-5-nitrobutyrophenone into 4-amino-2-methyl-5-methylaminobutyrophenone may also be carried out as follows and here it is also possible to use a crude isomer mixture as starting material.

241 g of crude chloromethylnitrobutyrophenone (approximately 70% of 4-chloro-2-methyl-5-nitrobutyrophenone) are suspended in 1200 ml of ethanol, and 1200 ml of 33% methylamine solution are added, whereupon dissolution takes place exothermically. The solution is allowed to stand for 2 days, is evaporated to dryness under reduced pressure, 100 ml of 2 N hydrochloric acid are added and the mixture is heated for 1 hour at 80° to 90°. The mixture is cooled to approximately 15° by the addition of ice, the crystalline precipitate is suction-filtered, subsequently washed with water, taken up in methylene chloride, dried over sodium sulphate, the methylene chloride is evaporated off under reduced pressure, at the end with the addition of cyclohexane and petroleum ether (boiling range 60°–80°), cooling is carried out and the 2-methyl-4-methylamino-5-nitrobutyrophenone, which melts at 105°–107°, is suction-filtered.

59.1 g of 2-methyl-4-methylamino-5-nitrobutyrophenone are dissolved in 1000 ml of methanol, 6 g of Raney nickel are added and hydrogenation is carried out at 20°–25° under normal pressure. After 16.8 liters of hydrogen have been absorbed, the hydrogenation is broken off, the mixture is gently heated to dissolve the precipitate, filtered off from the catalyst, 50 ml of concentrated hydrochloric acid are added, the mixture is cooled to 3° and suction-filtered. 4-amino-2-methyl-5-methylaminobutyrophenone hydrochloride is obtained having a melting point of above 180° (decomposition).

A mixture of 9.8 g of 5-amino-2-methyl-4-methylaminobutyrophenone and 4.15 g of glycolic acid is heated in an oil bath at 130° C. After 150 minutes, the reaction product, together with the product of a second batch of 3 g of 5-amino-2-methyl-4-methylaminobutyrophenone and 1.27 g of glycolic acid, is taken up in 300 ml of 2 N hydrochloric acid and filtered. The filtrate is rendered alkaline. The oil precipitated is extracted with three portions of ethyl acetate, the organic extract is washed twice with water, dried, filtered and concentrated by evaporation. The brown, oily residue crystallises spontaneously and is recrystallised from ethyl acetate. The 5-butyryl-1,6-dimethylbenzimidazole-2-methanol obtained in this manner melts at 141.5°–142.5°.

EXAMPLE 2

2.0 g of 5-butyryl-2-dichloromethyl-1,6-dimethylbenzimidazole are dissolved in 100 ml of ethanol. 50 ml of a 4 N sodium acetate solution are added and the solution is refluxed for 5 hours. The solution is evaporated to dryness under reduced pressure and recrystallised from ethyl acetate/cyclohexane. 5-butyryl-1,6-dimethylbenzimidazole-2-carboxaldehyde having a melting point of 116°–118° is obtained.

The starting material may be prepared, for example, as follows:

2.06 g of 3-amino-2-methyl-4-methylaminobutyrophenone are dissolved in 40 ml of 6 N hydrochloric acid, 2.6 g of dichloroacetic acid are added and the solution refluxed for 5 hours. The solution is allowed to cool, is diluted with water and extracted with methylene chloride. On concentrating the extract by evaporation the 5-butyryl-2-dichloromethyl-1,6-dimethylbenzimidazole remains in the form of a honey-like substance.

EXAMPLE 3

In a manner analogous to that described in Examples 1 and 2, the following may also be prepared:
5-acetyl-1-methylbenzimidazole-2-carboxaldehyde,
5-butyryl-1-methylbenzimidazole-2-carboxaldehyde,
1,6-dimethyl-5-valerylbenzimidazole-2-carboxaldehyde,
1-ethyl-5-butyryl-6-methylbenzimidazole-2-carboxaldehyde,
5-acetyl-1-butylbenzimidazole-2-carboxaldehyde,
1-butyryl-5-butyryl-6-methylbenzimidazole carboxaldehyde,
5-cyclopropylcarbonyl-1,6-dimethylbenzimidazole-2-carboxaldehyde,
5-butyryl-6-methylbenzimidazole-2-carboxaldehyde,
5(6)-valeroylbenzimidazole-2-carboxaldehyde,
5-valeroyl-6-methylbenzimidazole-2-carboxaldehyde,
5(6)-butyrylbenzimidazole-2-carboxaldehyde,
5-butyryl-6-methoxybenzimidazole-2-carboxaldehyde,
5-butyryl-6-chlorobenzimidazole-2-carboxaldehyde,
5-acetyl-6-methylbenzimidazole-2-carboxaldehyde,
5-propionyl-6-methylbenzimidazole-2-carboxaldehyde,
5-cyclohexylcarbonyl-6-methylbenzimidazole-2-carboxaldehyde,
5-(4-methoxybutyryl)-6-methylbenzimidazole-2-carboxaldehyde,
5-(4-methylthiobutyryl)-6-methylbenzimidazole-2-carboxaldehyde,
5-(4-methylsulphinylthiobutyryl)-6-methylbenzimidazole-2-carboxaldehyde,
5-(4-phenylthiobutyryl)-6-methylbenzimidazole-2-carboxaldehyde,
5-(4-phenylsulphinylbutyryl)-6-methylbenzimidazole-2-carboxaldehyde,
5-propionyl-1,6-dimethylbenzimidazole-2-carboxaldehyde and
5-isobutyryl-1,6-dimethylbenzimidazole-2-carboxaldehyde.

EXAMPLE 4

A 2% aqueous solution of 5-butyryl-1,6-dimethylbenzimidazole-2-carboxaldehyde, suitable for inhalation, can be prepared as follows:

| Composition (for 100 ml) | |
|---|---|
| 5-butyryl-1,6-dimethylbenzimidazole-2-carboxaldehyde | 2.000 g |
| disodium salt of ethylenediaminetetraacetic acid (stabiliser) | 0.010 g |
| benzalkonium chloride (preservative) | 0.010 g |
| water, distilled | ad 100 ml |

The 5-butyryl-1,6-dimethylbenzimidazole-2-carboxaldehyde is dissolved in freshly distilled water with the addition of a solubiliser, for example polyethylene glycol, and to this solution are added the disodium salt of ethylenediaminetetraacetic acid and the benzalkonium chloride (a mixture of alkyldimethylbenzylammonium chlorides, in which alkyl contains from 8 to 18 carbon atoms). When the constituents have completely dissolved the resulting solution is made up with water to a volume of 100 ml, introduced into containers and sealed so as to be air-tight.

EXAMPLE 5

Capsules, suitable for insufflation, containing 0.025 g of 5-butyryl-1,6-dimethylbenzimidazole-2-carboxaldehyde may be prepared as follows:

| Composition (for 100 capsules) | |
|---|---|
| 5-butyryl-1,6-dimethylbenzimidazole-2-carboxaldehyde | 25.00 g |
| lactose, powdered | 25.00 g |

The 5-butyryl-1,6-dimethylbenzimidazole-2-carboxaldehyde and the lactose (ground as finely as possible) are mixed well with one another. The resulting powder is then sieved and 0.05 g portions are introduced into gelatin capsules.

EXAMPLE 6

Tablets containing 100 mg of 5-butyryl-1,6-dimethyl-benzimidazole-2-carboxaldehyde (active substance) can be prepared, for example, with the following composition:

| Composition | per tablet |
|---|---|
| active substance, for example 5-butyryl-1,6-dimethylbenzimidazole-2-carboxaldehyde | 100 mg |
| lactose | 50 mg |
| wheat starch | 73 mg |
| colloidal silica | 13 mg |
| talc | 12 mg |
| magnesium stearate | 2 mg |
| | 250 mg |

Preparation

The active substance is mixed with the lactose, a portion of the wheat starch and with the colloidal silica and the mixture forced through the sieve. A further portion of the wheat starch is made into a paste on a water bath with 5 times the quantity of water and the powder is kneaded with this paste until a slightly plastic composition is formed. The composition is then forced through a sieve having a mesh width of approximately 3 mm, dried and the dry granulate again forced through a sieve. The remaining wheat starch, the talc and magnesium stearate are added and mixed in. The resulting mixture is compressed to form 250 mg tablets having a groove or grooves for breaking.

EXAMPLE 7

In a manner analogous to that described in Examples 4 to 6, it is possible to prepare pharmaceutical preparations containing a compound according to one of claims 2 and 3.

We claim:

1. An antiallergical pharmaceutical preparation containing an effective amount of a compound of the formula

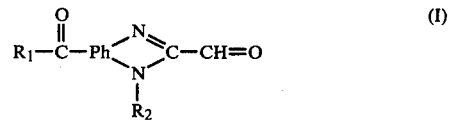

in which

R₁ represents lower alkyl having up to and including 7 carbon atoms; lower alkoxy-lower alkyl, lower alkylthio-lower alkyl, lower alkylsulphinyl-lower alkyl or lower alkylsulphonyl-lower alkyl, in which the individual lower alkyl radicals contain up to and including 4 carbon atoms; phenylthio-lower alkyl, phenylsulphinyl-lower alkyl or phenylsulphonyl-lower alkyl in which the lower alkyl radical contains up to and including 4 carbon atoms; lower alkenyl having up to and including 5 carbon atoms; cycloalkyl having up to and including 7 carbon atoms; phenyl or phenyl-lower alkyl having up to and including 4 carbon atoms in the lower alkyl radical and both optionally substituted by lower alkyl having up to and including 4 carbon atoms, by lower alkoxy having up to and including 4 carbon atoms, and/or by halogen having an atomic number of up to and including 35;

R₂ represents hydrogen or lower alkyl having up to and including 4 carbon atoms, and Ph represents 1,2-phenylene containing the radical of the formula R₁—C(=O)— and optionally substituted by lower alkyl having up to and including 4 carbon atoms, by lower alkoxy having up to and including 4 carbon atoms, hydroxy and/or by halogen having an atomic number of up to and including 35, together with customary pharmaceutical auxiliaries and carriers.

2. A pharmaceutical preparation according to claim 1, containing a compound of the formula

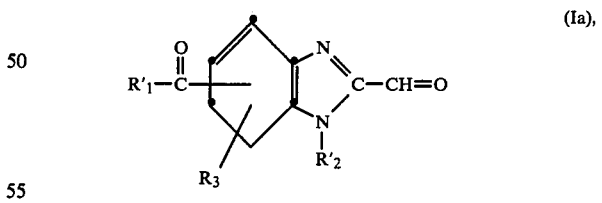

in which

R₁' represents lower alkyl having up to and including 7 carbon atoms, cycloalkyl having up to and including 6 ring carbon atoms or phenyl, R₂' represents hydrogen or lower alkyl having up to and including 4 carbon atoms, and R₃ represents hydrogen, lower alkyl having up to and including 4 carbon atoms or halogen having an atomic number of up to and including 35.

3. A pharmaceutical preparation according to claim 1, containing a compound of the formula

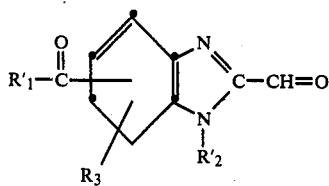

(Ia), in which
R₁' represents lower alkyl having up to and including 7 carbon atoms, and
R₂' and R₃ represent lower alkyl having up to and including 4 carbon atoms, the radical R₁'-C(=O)— occupying the 5-position of the benzimidazole ring and the lower alkyl radical R₃ occupying the 6-position of the benzimidazole ring.

4. A pharmaceutical preparation according to claim 1, containing the compound 5-butyryl-1,6-dimethylbenzimidazole-2-carboxaldehyde.

5. A pharmaceutical preparation according to claim 1, containing a compound selected from the group consisting of
5(6)-valerylbenzimidazole-2-carboxaldehyde,
5-butyryl-6-methylbenzimidazole-2-carboxaldehyde,
5-acetyl-6-methylbenzimidazole-2-carboxaldehyde,
6-methyl-5-propionylbenzimidazole-2-carboxaldehyde,
6-methyl-5-valerylbenzimidazole-2-carboxaldehyde,
5(6)-butyrylbenzimidazole-2-carboxaldehyde,
5-butyryl-6-methoxybenzimidazole-2-carboxaldehyde,
5-butyryl-6-chlorobenzimidazole-2-carboxaldehyde,
5-cyclopropylcarbonyl-1,6-methylbenzimidazole-2-carboxaldehyde,
5-cyclohexylcarbonyl-6-methylbenzimidazole-2-carboxaldehyde,
5-(4-methoxybutyryl)-6-methylbenzimidazole-2-carboxaldehyde,
6-methyl-5-(4-methylthiobutyryl)benzimidazole-2-carboxaldehyde,
6-methyl-5-(4-methylsulphinylbutyryl)benzimidazole-2-carboxaldehyde,
6-methyl-5-(4-phenylthiobutyryl)benzimidazole-2-carboxaldehyde,
6-methyl-5-(4-phenylsulphinylbutyryl)benzimidazole-2-carboxaldehyde,
5-acetyl-1-methylbenzimidazole-2-carboxaldehyde,
5-butyryl-1-methylbenzimidazole-2-carboxaldehyde,
1,6-dimethyl-5-valerylbenzimidazole-2-carboxaldehyde,
1-ethyl-5-butyryl-6-methylbenzimidazole-2-carboxaldehyde,
5-acetyl-1-n-butylbenzimidazole-2-carboxaldehyde,
1-n-butyl-5-butyryl-6-methylbenzimidazole-2-carboxaldehyde,
5-propionyl-1,6-dimethylbenzimidazole-2-carboxaldehyde and
5-isobutyryl-1,6-dimethylbenzimidazole-2-carboxaldehyde.

6. A pharmaceutical preparation as claimed in claim 1 which can be administered orally or by insufflation containing from approximately 5 to 90% by weight of a compound claimed in claim 1.

7. A pharmaceutical preparation as claimed in claim 1 which can be administered orally or by insufflation containing from approximately 10 to 60% by weight of a compound claimed in claim 1.

8. A pharmaceutical preparation as claimed in claim 1 which can be administered parenterally or by inhalation containing from approximately 0.5 to 20% by weight of a compound claimed in claim 1.

9. A pharmaceutical preparation as claimed in claim 1 which can be administered parenterally or by inhalation containing from approximately 1 to 5% by weight a compound claimed in claim 1.

* * * * *